United States Patent
Young et al.

(10) Patent No.: US 9,617,515 B2
(45) Date of Patent: Apr. 11, 2017

(54) NON-EMBRYONIC TOTIPOTENT BLASTOMERE-LIKE STEM CELLS AND METHODS THEREFOR

(75) Inventors: Henry E. Young, Macon, GA (US); Asa Black, El Paso, TX (US)

(73) Assignee: Moraga Biotechnology Corporation, Los Angeles, CA (US)

(*) Notice: Subject to any disclaimer, the term of this patent is extended or adjusted under 35 U.S.C. 154(b) by 2723 days.

(21) Appl. No.: 12/280,833

(22) PCT Filed: Feb. 27, 2007

(86) PCT No.: PCT/US2007/005142
§ 371 (c)(1),
(2), (4) Date: Jan. 26, 2009

(87) PCT Pub. No.: WO2007/100845
PCT Pub. Date: Sep. 7, 2007

(65) Prior Publication Data
US 2009/0186334 A1    Jul. 23, 2009

Related U.S. Application Data

(60) Provisional application No. 60/777,572, filed on Feb. 27, 2006, provisional application No. 60/779,842, filed on Mar. 6, 2006, provisional application No. 60/779,841, filed on Mar. 6, 2006, provisional application No. 60/779,997, filed on Mar. 6, 2006, provisional application No. 60/779,992, filed on Mar. 6, 2006.

(51) Int. Cl.
| | |
|---|---|
| *C12N 15/00* | (2006.01) |
| *C12N 5/0789* | (2010.01) |
| *C12N 5/074* | (2010.01) |
| *C12N 5/078* | (2010.01) |
| *C12N 5/0735* | (2010.01) |

(52) U.S. Cl.
CPC ......... *C12N 5/0647* (2013.01); *C12N 5/0607* (2013.01); *C12N 5/0606* (2013.01); *C12N 5/0634* (2013.01)

(58) Field of Classification Search
CPC ... C12N 5/0607; C12N 5/0606; C12N 5/0634
See application file for complete search history.

(56) References Cited

U.S. PATENT DOCUMENTS

| | | |
|---|---|---|
| 5,874,301 A | 2/1999 | Keller et al. |
| 6,107,543 A | 8/2000 | Sims et al. |
| 6,703,209 B1 | 3/2004 | Baetscher |
| 2003/0161817 A1 | 8/2003 | Young et al. |
| 2003/0161818 A1 | 8/2003 | Weiss et al. |
| 2003/0175955 A1 | 9/2003 | Keller et al. |
| 2004/0033214 A1 | 2/2004 | Young et al. |

FOREIGN PATENT DOCUMENTS

| | | |
|---|---|---|
| EP | 1176187 | 1/2002 |
| WO | 9516770 | 6/1995 |
| WO | 9720035 | 6/1997 |
| WO | 0121767 | 3/2001 |
| WO | 0231123 | 4/2002 |

OTHER PUBLICATIONS

Yao et al. In vitro cultivation of human fetal pancreatic ductal stemcells and their differentiation into insulin-producing cells. World J Gastroenterol., 2004, vol. 10, pp. 1452-1456.*
Brown et al. Effect of cryosurgery on liver blood flow. British J. Cancer, 1993, vol. 68, pp. 10-12.*
Donda et al. Locally inducible CD66a (CEACAM1) as an amplifier of the human intestinal T cell response. European J. Immunol., 2000, vol. 30, pp. 2593-2603.*
Young, H.E. Chapter 9: Stem Cells and Tissue Engineering, pp. 143-173, In: Gene therapy and tissue engineering in orthapaedic and sports medicine. Methods in Bioengineering (Series). Johnny Huard and Freddie H. Fu, eds., Birkhauser: Boston, 2000.*
Young et al. Clonogenic Analysis Reveals Reserve Stem Cells in Postnatal Mammals. II. Pluripotent Epiblastic-Like Stem Cells. Anatomical Record Part A, 2004, vol. 277A, pp. 178-203.*
Schwartz et al. Multipotent adult progenitor cells from bone marrow differentiate into functional hepatocyte-like cells. Journal of Clinical Investigation, 2002, vol. 109, pp. 1291-1302.*
Jiang et al. Multipotent progenitor cells can be isolated from postnatal murine bone marrow, muscle, and brain. Experimental Hematology, 2002, vol. 30, pp. 896-904.*
Schulz et al. Stem cells isolated from adult rat muscle differentiate across all three dermal lineages. Wound Repair and Regeration, 2006, vol. 14, pp. 224-231.*
Young, et al., Adult Reserve Stem Cells and Their Potential for Tissue Engineering, Cell Biochemistry and Biophysics, vol. 40, 2004.
Young, et al., Adult Stem Cells, The Anatomical Record Part A 276A:75-102, 2004.

* cited by examiner

*Primary Examiner* — Deborah Crouch
(74) *Attorney, Agent, or Firm* — Fish & Tsang LLP

(57) ABSTRACT

Human non-embryonic adult totipotent and pluripotent stem cells are isolated in a simplified serum-free and feeder cell-free process. Most remarkably, certain stem cells, and especially BLSCs, are extremely small, fail to exclude trypan blue, but are nevertheless able to proliferate from even high dilutions. Therefore, so obtained stem cells can be used to prepare true monoclonal stem cell populations, which are useful in numerous uses, including therapeutic, prophylactic, diagnostic, and research uses.

6 Claims, No Drawings

NON-EMBRYONIC TOTIPOTENT BLASTOMERE-LIKE STEM CELLS AND METHODS THEREFOR

This application claims priority to our copending U.S. provisional patent applications with the Ser. Nos. 60/777,572 filed Feb. 27, 2006, 60/779,842, 60/779,841, 60/779,997, and 60/779,992 all filed Mar. 6, 2006, and further relates to our International application with the serial number PCT/US05/30284 filed Aug. 25, 2005, all of which are incorporated by reference herein.

FIELD OF THE INVENTION

The field of the invention is stem cells and reagents for same, and especially as they relate to totipotent non-embryonic stem cells.

BACKGROUND OF THE INVENTION

Stem Cells

It is currently thought that mammalian cells progress from embryonic cell stages to fully developed cells through a defined sequence of events. Totipotent blastomere cells develop into pluripotent epiblast cells, which develop into germ layer lineage cells, which give rise to multipotent progenitor cells that develop to tripotent, then bipotent, then unipotent progenitor cells, and finally to the differentiated cell types.

Remarkably, while the vast majority of cells progress through that sequence of development and differentiation, a few cells become reserve precursor cells that provide for continual maintenance and repair of the organism. Known reserve precursor cells located within the postnatal individual include epiblast-like stem cells, germ layer lineage stem cells (ectodermal germ layer lineage stem cells, endodermal germ layer lineage stem cells, and the mesodermal germ layer lineage stem cells), and various progenitor cells. In recent years, particular interest focused on early-stage cells, and especially embryonic stem cells.

Embryonic stem cells (ESCs) are uncommitted cells isolated from embryonic tissues. For example, ESCs are commonly isolated from the blastocyst, inner cell mass, and gonadal ridges of mouse, rabbit, rat, pig, sheep, primate, and human embryos. When injected into embryos, ESCs can give rise to all somatic lineages as well as functional gametes (i.e., sperm cells). ESCs typically spontaneously differentiate in serum-free defined medium in the absence of agents that inhibit differentiation (e.g., leukemia inhibitory factor). Further known embryonic stem cell preparations from embryoid tissue, post-morula tissue, blastocyst stage and pre-blastocyst stage were described in U.S. Pat. App. No. 2003/0175955, EP 1 176 189, WO 1997/020035, and WO 1995/016770, respectively. However, such cell preparations are either pluripotent and/or isolated from an embryo, which is ethically controversial. Totipotent bovine embryonic stem cells have been reported in U.S. Pat. No. 6,107,543, and ungulate germ-line forming stem cells (possibly not totipotent) have been described in U.S. Pat. No. 6,703,209.

In still further known methods, pluripotent stem cells have been isolated from non-embryonic sources, including from umbilical cord matrix as described in U.S. Pat. App. No. 2003/0161818 and postnatal gonadal tissue as taught in WO 2002/031123. However, while such cells do not require destruction of an embryo and are therefore potentially of interest for human stem cells, the so isolated stem cells have not been demonstrated to be totipotent.

Upon differentiation in vitro all or almost all of these embryonic cells express a wide variety of cell types, including gametes, as well as cells derived from the ectodermal, mesoderm, and endodermal germ layer lineages. Unfortunately, when currently known uncommitted embryonic stem cells are implanted into animals, they typically spontaneously differentiate in situ, forming teratomas. These tumors contain various types of cells and tissue derived from all three primary germ layer lineages (Thomson et al., 1988). Therefore, while ESCs appear to have therapeutic potential in transplantation therapies, their tendency to differentiate spontaneously in an uncontrolled manner places limitations on their usefulness.

Stem Cell Propagation

Growth medium for most stem cells grown in culture is routinely supplemented with animal and/or human serum to optimize and enhance cell viability. The constituents of serum include water, amino acids, glucose, albumins, immunoglobulins, and one or more bioactive agents. Potential bioactive agents present in serum include agents that induce proliferation, agents that accelerate phenotypic expression, agents that induce differentiation, agents that inhibit proliferation, agents that inhibit phenotypic expression, and/or agents that inhibit differentiation. Unfortunately, the identity(ies), concentration(s), and potential combinations of specific bioactive agents contained in different lots of serum is/are unknown. One or more of these unknown agents in serum have shown a negative impact on the isolation, cultivation, cryopreservation, and purification of lineage-uncommitted blastomere-like stem cells. Similarly, where feeder layers for embryonic stem cells were employed, contamination of stem cell cultures with feeder layer specific components, and especially viruses frequently occurs.

Alternatively, serum-free media are known for general cell culture, and selected pluripotent stem cells have been propagated in such medium containing a plurality of growth factors as described in US20050164380, US20030073234, U.S. Pat. No. 6,617,159, U.S. Pat. No. 6,117,675, or EP1298202.

Stem Cell Isolation

All or almost all of currently known cell isolation protocols from native tissue or tissue samples rely on selective cultivation, and typically involve separation steps with cell surface markers to obtain an enriched culture. While such known protocols are often satisfactory for most purposes, various difficulties remain where the isolated cells are stem cells. Among other things, media for stem cells often contain serum or other poorly defined ingredients that tend to either block growth and/or induce stem cells to more committed progenitor cells of different lineages. In certain instances, serum free media have been reported for stem cell cultivation. However, such media are generally limited to specific stem cells and cannot be transferred from one cell line to the next.

Regardless of the manner of isolation, truly monoclonal stem cell populations derived from a single cell and with at least totipotent (and more desirably pluripotent) characteristics have not been achieved as dilution of heretofore known stem cells reduced viability and/or proliferation. Such lack of true monoclonal stem cell lines significantly complicates their characterization and use. Their response to various stimuli and/or specific environment will be less than uniform. As a result, identification of particular effects of selected compounds on a stem cell population is generally not reliable, or even possible.

Thus, while numerous compositions and methods for stem cells are known in the art, all or almost all of them suffer from one or more disadvantages. Therefore, there is still a need for improved stem cells, compositions, and reagents for their production, maintenance, and differentiation, and especially for postnatal totipotent blastomere-like stem cells.

SUMMARY OF THE INVENTION

The present invention is directed to compositions and methods related to adult non-embryonic stem cells that are pluripotent, and more typically totipotent. Most advantageously, the stem cells presented herein are isolated in a very simple process that avoids use of serum and feeder cells. Among other remarkable features, the stem cells according to the inventive subject matter lack trypan blue exclusion but are viable in certain media, which typically use a carbohydrate source other than glucose.

Therefore, in one aspect of the inventive subject matter, a preparation includes an isolated cell characterized by (a) pluripotent or totipotent character, (b) average size of equal or less than 5.0 micrometer, (c) refractile appearance under phase contrast, (d) lack of trypan blue exclusion, and (e) viability to proliferate in serum-free medium.

Preferably, the isolated cell is a suspended blastomere-like stem cell (BLSC), an adherent BLSC, a transitional BLSC, and/or an epiblast-like stem cell (ELSC), and most preferably the isolated cell is a human cell, which is typically characterized by the surface markers CEA-CAM-1$^+$, SSEA-1$^-$, SSEA-3$^-$, and SSEA-4$^-$. In most instances, the cell has an average size of equal or less than 2.5 micrometer, and more typically 2.5 micrometer and may be further characterized by replication as an adherent cell. Where the cell has an average size of equal or less than 1.0 micrometer, the cell is further characterized by replication as a suspended cell. In further especially contemplated aspects, the serum-free medium has a carbohydrate source other than glucose. Where the preparation is an intermediate in the isolation, the preparation will typically further comprise additional cells, wherein at least 50% of the additional cells are not viable, wherein the additional cells and the isolated cell form a tissue.

Viewed from a different perspective, a preparation comprising a monoclonal cell or a monoclonal cell population in serum-free medium, wherein the cell or cell population has pluripotent or totipotent character, lacks trypan blue exclusion, and is viable to proliferate in serum-free medium.

Most preferably, the cell or cell population is a human cell or cell population, and the cells have an average size of equal or less than 5.0 micrometer. In further preferred aspects, the serum-free medium has a carbohydrate source other than glucose. Where desirable, the cell or cell population is disposed within a matrix, and/or may be disposed in a plurality of wells of a multiwell plate.

In still further contemplated aspects, the inventors contemplate a method of isolating a pluripotent or totipotent stem cell that lacks trypan blue exclusion and is viable to proliferate in serum-free medium that includes a step of providing a tissue sample and placing the tissue sample into a first serum-free medium. In a further step, the tissue sample is incubated for a time sufficient to (a) allow non-stem cells in the tissue sample to die and to (b) maintain viability of the stem cell in the sample, and in a still further step, the tissue is processed in a second serum-free medium to enrich or isolate the stem cell, wherein first and second serum-free media employ a carbohydrate source other than glucose.

In preferred aspects, the tissue sample comprises whole blood or mechanically and enzymatically treated solid tissue. Where the incubation time is at least 5 days at about 4° C., ELSC are enriched or isolated, and where the incubation time is at least 7 days at about 4° C., adherent BLSC are enriched or isolated. Furthermore, where the incubation time is at least 9 days at about 4° C., suspended BLSCs are enriched or isolated.

Various objects, features, aspects and advantages of the present invention will become more apparent from the following detailed description of preferred embodiments of the invention.

DETAILED DESCRIPTION

The inventors have surprisingly discovered that BLSCs and other stem cells can be isolated from various tissues using a protocol that allows enrichment and/or specific isolation of a stem cell in a manner independent of cultivation steps and/or cell surface marker-based techniques. Such stem cells are isolated and selected for by several unique and unexpected characteristics heretofore not described. Among other things, the stem cells according to the inventive subject matter can be characterized by their pluripotent or totipotent character, average size of equal or less than 5.0 micrometer, their refractile appearance under phase contrast, their lack of trypan blue exclusion, and their viability to proliferate in serum-free medium.

In one preferred aspect of the inventive subject matter, the inventor discovered that BLSCs and other stem cells can be isolated from human and non-human tissues (e.g., porcine, equine, rodent, etc) that is not only technically and/or conceptually simple, but also significantly shortens the time between sample procurement and final stem cell product.

In one exemplary aspect, the stem cell is a BLSC and is isolated from human blood, typically by venipuncture. Here, about 1 ml of whole blood is obtained and stored with EDTA or other $Ca^{2+}$ complexing agent for about 9 days in transport medium at a temperature of about 4° C. (e.g., using Moraga medium with catalog number MBC-HUB-MED-100-A004 (human), MBC-RTB-MED-100-A004 (rat), MBC-MOB-MED-100-A004 (mouse), or MBC-PGB-MED-100-A004 (porcine). After 9 days, the red cells in the whole blood sample are then lysed using about 50 ml of sterile hemolysis solution (MBC-ASB-REBG-900A-001, Moraga Biotechnology Corporation, Los Angeles, Calif.). After centrifugation under conditions sufficient to remove debris and lysed cells from the remaining intact stem cells (e.g., at 1800×g, 10 min.), the cell pellet is resuspended in 2 ml of Moraga sterile reconstitution solution (MBC-ASB-REBG-900A-002), the intact cells are then further purified with 48 ml Moraga clarification solution (MBC-ASB-REBG-900A-003) (e.g., 1800×g, 10 min), the stem cell-containing pellet is taken up in 3-5 ml of appropriate medium (e.g., Moraga infusion solution with catalog number MBC-HUB-REBG-900A-004 (human), MBC-PGB-REBG-900A-005 (porcine), MBC-RTB-REBG-900A-006 (rat), MBC-MOB-REBG-900A-007 (mouse), Moraga serum-free defined culture medium MBC-HUB-MED-1A00-A006 (human), MBC-RTB-MED-1A00-A006 (rat), MBC-MOB-MED-1A00-A006 (mouse), MBC-PGB-MED-1A00-A006 (porcine), or Moraga base medium with catalog number MBC- HUB-MED-100-A002 (human), MBC-RTB-MED-100-A002 (rat), MBC-MOB-MED-100-A002 (mouse), or MBC-PGB-MED-100-A002 (porcine) and then cryopreserved at −80° C.+/−5° C. (MBC-HUB-MED-100-A005 (human), MBC-RTB-MED-100-A005 (rat), MBC-MOB-MED-100-A005 (mouse), or MBC-PGB-MED-100-A005 (porcine)), or plated at a desired density in an adult stem cell substrate-coated culture vessel, e.g., T75-cm$^2$ flasks (MBC-HUB-MSC-900-A006 (human, clinical), MBC-ASB-MSD-900-A006 (diagnostic)), T25-cm$^2$ flasks (MBC-HUB-MSC-900-A007 (human, clinical), MBC-ASB-MSD-900-A007 (diagnostic)), 6-well plates (MBC-HUB-MSC-900-A008 (human, clinical), MBC-ASB-MSD-900-A008 (diagnostic)), 24-well plates (MBC-HUB-MSC-900-A009 (human, clinical), MBC-ASB-MSD-900-A009 (diagnostic)), 48-well plates (MBC-HUB-MSC-900-A010 (human, clinical), MBC-ASB-MSD-900-A010 (diagnostic)), or 96-well plates (MBC-HUB-MSC-900-A011 (human, clinical), MBC-ASB-MSD-900-A011 (diagnostic)).

Remarkably, as storage of the whole blood in the transport medium progressed over a period of several days, the inventors discovered that viability of certain types of stem cells was a function of storage time. More specifically, the inventors observed that viability of cells dropped in the following order: Differentiated cells lost viability after 1 day, progenitor cells lost viability after 2 days, GLLSCs lost viability after 3 days, ELSCs lost viability after 5 days, and BLSCs lost viability after 10 days, or even longer. In should be especially noted that the so stored cells were not cultivated during storage, and that the observed loss of viability within the sampled tissue occurred without external influence (for cell nomenclature, see Table 1, Cancer Gene Mechanisms And Gene Therapy, Minerva Biotech (2005), Vol. 17, No. 2, H. Young and A. Black, incorporated by reference herein).

Of course, it should be appreciated that the drop in viability may vary to some degree, depending on the storage temperature (preferably between 2° C. and 12° C., more preferably about 4° C.). Thus, it should be especially appreciated that by simply storing a mixed population of mammalian, and especially human cells in transport medium, substantially pure (i.e., greater 90%, more typically greater 95%) and mostly viable BLSC populations can be obtained. Even more remarkably, such obtained BLSC populations may be further differentiated (between adherent and suspended stages) using additional storage time. Consequently, mixed BLSC populations may be obtained using storage periods intermediate to those required for adherent and suspended BLSCs. So obtained stem cells (e.g., BLSCs, ELSCs) may therefore be mixed populations, which can be separated and/or processed using various protocols described herein and/or well known in the art (e.g., using surface markers, viability in transport medium, etc.). Most typically, separation of so isolated stem cells is then performed using size as discriminating factor (e.g., in a dielectric field). Furthermore, where it is desired that the cell population also includes ELSCs (and/or other more differentiated stem cells), shortened storage periods and optionally no separation are also contemplated.

In alternative aspects of the inventive subject matter, it should be recognized that the starting material need not be limited to whole blood, but that in fact all vertebrate, mammalian, and especially human tissues are deemed suitable for use herein. For example, numerous solid tissues may be employed, including skin, liver, kidney, pancreas, muscle tissue, adipose tissue, bone marrow, neural tissue, etc. Thus, it should be appreciated that the stem cells are isolated from a mammal or human (e.g., biopsy or phlebotomy) without killing the mammal or human. It should also be noted that where solid tissues are used, it is generally preferred that the sample is first stored in the transport medium in relatively small tissue pieces (e.g., pieces with largest dimensions of less than 5 mm$^3$) for a predetermined period of time (e.g., 5 days), after which the tissue is further disintegrated (e.g., using scalpel or scissors) and optionally enzymatically digested. Most commonly, enzymatic digestion is performed using Moraga enzymatic release solution with catalog numbers MBC-HUB-REC-100-A003 (human, clinical), MBC-HUB-RED-100-A003 (human, diagnostic), MBC-RTB-RED-100-A003 (rat), MBC-MOB-RED-100-A003 (mouse), MBC-PGB-RED-100-A003 (porcine). Enzymatic treatment follows generally known procedures and is typically finished after between 5 and 1440 minutes. It should be noted that the particular arrangement of the extracellular matrix from which the tissue sample is taken will dictate the length of digestion. The more tightly compacted the extracellular matrix, the longer the incubation time with the enzymatic release solution. Usually, compactness of the ECM relates directly to age of the individual, but not necessarily so. Digestion times can be as long as overnight if the individual is older than 80 years of age. The so obtained cell-containing solution is optionally filtered, and the solution is replaced with appropriate medium for cultivation or storage as desired.

On the other hand, where whole blood is a preferred source of the stem cells, the blood sample may be partially processed to remove red blood cells, or other whole blood components. Further, less preferred sources include body fluids other than whole blood such as peritoneal fluid, spinal fluid, etc.

It is further contemplated that the medium for transport of the cells or tissue may be modified, and that alternative media especially include isotonic, buffered media (typically pH 7.2 to 7.4) with one or more reductants (e.g., mercaptoethanol, spermidine, putrescine), or glycol, protease inhibitors, nutrients (e.g., amino acids and carbohydrates, etc). While not limiting to the inventive subject matter, it is generally preferred that the cells or tissue are maintained under reduced oxygen conditions (e.g., less than 5% O$_2$).

Additionally or alternatively, crude, enriched, and/or isolated cell populations may also be (preferably selectively) concentrated using magnetic beads, dielectric field isolation, microfluidic separation, Ficoll gradients, one or more steps of filtration in which larger cells are separated from smaller cells, etc. In this context, it is especially noted that the BLSC (both adherent and suspended) will typically have a size of less than 5 micrometer. Under most circumstances, BLSCs isolated using the procedures according to the inventive subject matter will have a size of between less than 2 micrometer (in some cases as small as 0.1 micrometer) to about 5 micrometer. Such small cells typically stain positive for trypan blue where the cells are smaller than 3 micrometer. As the adherent BLSCs develop into ELSCs, trypan blue staining is typically lost, with the area of the cytoplasm adjacent to the plasma membrane loosing the stain last.

Alternative storage temperatures include those between 0° C. and 37° C., more typically between 2° C. and 25° C., and most typically between 4° C. and 12° C. Thus, and dependent on the particular medium and storage temperature, contemplated isolation by negative selection may occur in a shorter time frame (e.g., BLSC loss of viability in 7 days at higher temperatures), or longer time frame (e.g., BLSC loss of viability in 12 days at lower temperatures).

In a further alternative protocol, the BLSCs (or other downstream stem cells derived from BLSCs) are isolated from human blood. Here, about 1 ml of whole blood is obtained and red cells are lysed using about 50 ml of Hemolysis solution (Moraga catalog number MBC-ASB-REBG-900A-001). After centrifugation under conditions sufficient to remove debris and lysed cells from cells remaining cells (e.g., 2000×g, 5 min.), and optional repeat of the lysis and centrifugation, the remaining stem cell-containing pellet is taken up in 3-5 ml of storage medium (catalog number MBC-HUB-MED-100-A005 (human), MBC-RTB-MED-100-A005 (rat)), typically in a 50 ml conical tube, and are then plated in a T75 culture flask. The so suspended cells are then placed in a refrigerator and kept at a temperature of about 4° C.

Remarkably, and as already observed above, the inventors discovered that viability of certain types of stem cells was a function of storage time. More specifically, the inventors observed that viability of cells dropped in the following order: Differentiated cells (loss of viability after 1 day), progenitor cells (loss of viability after 2 days), GLLSCs (loss of viability after 3 days), ELSCs (loss of viability after 5 days), adherent BLSCs (loss of viability after 8 days), suspended BLSCs (loss of viability after 10 days or longer). In should again be noted that the so stored cells were not cultivated during storage, and that loss of viability occurred without external influence. Thus, mixed BLSC populations may be obtained using storage periods intermediate to those required for adherent and suspended BLSCs. These and other mixed populations may then be separated and/or processed using protocols well known in the art (e.g., using surface markers). Furthermore, where it is desired that the cell population also includes ELSCs (and/or other more differentiated stem cells), shortened storage periods are contemplated.

When isolated, selected, and/or cultured using the serum-free media (which most preferably also has a carbohydrate source other than glucose [e.g., mannose, maltose, sorbose, ribose, ribulose, fructose, tagatose, galactose, gulose, etc.]), the inventors discovered that the non-embryonic stem cells, and especially BLSCs can be identified and characterized by using various highly unusual structural and metabolic properties. Most significantly, BLSCs according to the inventive subject matter are typically less than 5 micrometer. Typically, suspended BLSCs are generally between 0.1 micrometer and 1 micrometer, while adherent BLSCs are often between 1 micrometer and 3 micrometer, and in some cases up to 5 micrometer. Such measurements refer to the average size of a population of cells with respect to their longest dimension.

For example, in one especially preferred aspect, the stem cell is a BLSC, which may be adherent or in suspension, or a cell intermediate to a BLSC and an ELSC (epiblast-like stem cell) (also termed "transition cell" for its stage between a BLSC and an ELSC). Selected characteristics of such cells are listed in the table below, in which suspended BLSCs are denoted sBLSCs, adherent BLSC are denoted aBLSCs, and intermediate cells between BLSC and ELSC are denoted transitional BLSCs (trBLSCs).

| Marker | sBLSCs | aBLSCs | trBLSCs |
|---|---|---|---|
| Size | 0.1 to 1.0 µm | 1.0 to 2.5 µm | 2.5 to 5.0 µm |
| Trypan Blue Stain | Positive | Positive | Membrane positive, center negative |

-continued

| Marker | sBLSCs | aBLSCs | trBLSCs |
|---|---|---|---|
| Appearance under phase contrast | Refractile, bright center, defined edge, generally round | Refractile, bright center, defined edge, generally round with occasional processes | Refractile, bright, defined edge, generally round with occasional processes |
| Replication Apparent Chromatin Structure | While suspended Heterochromatin | While adherent Heterochromatin | While adherent Heterochromatin |

Still further, BLSCs isolated and/or cultivated as above are easily identified using a phase contrast microscope. Under proper illumination and instrument settings, all types of BLSCs will present as refractile small cells (either suspended or adherent) having a size between less than 0.1 micrometer and about 5 micrometer. Such small size and refractile appearance is rather unexpected as ordinarily objects presenting themselves in this manner are debris or other non-cellular structures. It should be noted that where the medium includes $Ca^{2+}$, BLSCs will tend to agglomerate. Also, to facilitate adhesion of BLSCs the medium preferably includes fibronectin, which will bond to the RGD sites on the aBLSCs, thus allowing adhesion to collagen plated substrates. Most preferably, the defined serum-free media include a non-glucose carbohydrate (preferably a monosaccharide, and most preferably a hexose), putrescine, beta-mercaptoethanol, cholesterol, fatty acids, amino acids, gelatin, and fibronectin.

Yet another unusual property of cells isolated, enriched, and/or cultivated cells as described herein is their lack of trypan blue exclusion. It should be especially noted out that Trypan Blue is a dye that is ordinarily used to determine the viability of a cell. In known protocols, it is categorically assumed that living cells exclude the trypan blue dye, whereas dead cells will retain the trypan blue dye. In contrast, the cells presented herein do not exclude the trypan blue dye, but are nevertheless viable as evidenced by their proliferation in serum-free defined medium. Such finding is highly unusual, as trypan blue positive cells are considered non-viable in the art.

Even more remarkably, each of the above BLSCs can be propagated as true clonal stem cells (i.e., a population of cells originates from a single isolated cell). Indeed, a population of BLSCs can be diluted to a degree such that an individual BLSC can be isolated in well or small dish, and that that so isolated cell will then give rise to a true monoclonal population of stem cells. Most typically, BLSCs can be grown from very low seeding densities, and even from single cells using conditioned BLSC media. Such discovery is particularly noteworthy as this is the first reported true monoclonal stem cell culture (and especially in serum free defined medium). In contrast, heretofore known 'clonal' stem cell cultures were obtained from a plurality of seeded cells (at least 4 or more cells). Consequently, for the first time, a true monoclonal stem cell population is available, which will greatly facilitate research into conditions that trigger differentiation or other cellular responses.

BLSCs according to the inventive subject matter are preferably grown under reduced oxygen atmosphere using a carbohydrate source other than glucose (as the BLSCs likely do not produce G6PDH). Most typically, a non-glucose monosaccharide (most preferably a hexose) may be employed as a preferred alternative carbohydrate source.

Among other preferred options, low oxygen is typically realized by growing the cells in a medium with one or more reducing agents, including β-mercaptoethanol, putrescein, spermidine, etc. It should be noted that the metabolic state of such BLSCs is very close to a resting state or inactive state. Therefore, it is contemplated that the BLSCs are generally less sensitive to agents and/or conditions adverse to a metabolically active cell (e.g., myocyte, fibroblast, hepatocyte, etc.). For example, BLSCs can be maintained in a viable state in the absence of glucose and at a relatively low oxygen content in the medium (or embedded in tissue). Most preferably, BLSCs are stored in cryopreservation medium (e.g., using Moraga medium with catalog number MBC-HUB-MEC-100-A005 (human, clinical), MBC-HUB-MED-100-A005 (human, diagnostic), MBC-RTB-MED-100-A005 (rat), MBC-MOB-MED-100-A005 (mouse), MBC-PGB-MED-100-A005 (porcine)) at a temperature between −70° C. and −90° C., and most preferably at −80° C., while GLSCs are preferably stored at a temperature between −60° C. and −80° C., most preferably at −70° C.

Moreover, and based on the remarkable resiliency of the BLSCs, it is further contemplated that BLSCs can be maintained in an at least partially dehydrated environment, or in a non-liquid medium. For example, it is contemplated that BLSCs can be lyophilized or otherwise dehydrated (e.g., spray-dried), which may or may not be performed in the presence of a freeze-dry preservant (e.g., lactose) well known in the art. In further examples, it is contemplated that the BLSCs can be maintained (e.g., at room temperature, about 20° C.) in a gelled medium that is gelled at room temperature and that liquefied at about 33° C. to 37° C. Such media can be prepared, for example, by adding gelatin or other gelling medium to the transport medium at a concentration effective to gel the medium at a desired temperature (see below). Such preserved BLSC preparations may then be used in or on medical devices that are placed in contact with a diseased, aged, or otherwise non-healthy tissue. Additionally, such preserved BLSC preparations may then be used in microtiter plates of varying density for cell-based analysis.

Among numerous other characteristics, it should also be noted that all types of BLSCs as indicated in the table above are deemed totipotent. Thus, the BLSCs will give rise to all known tissue types, including placental tissue, and reproductive tissue (e.g., spermatogonial and/or oogonial cells). In terms of development of such cells, it is especially pointed out that the BLSCs upon proper culture conditions will typically progress from a small size (e.g., between 0.5 micrometer to about 5 micrometer) to a larger size, before developing into an ELSC, which then in turn and again under appropriate stimulation develop into a GLLSCs (germ layer lineage stem cells). In one exemplary developmental progression, suspended BLSCs (currently the most undifferentiated stem cells; most likely totipotent) develop (likely irreversibly) into adherent, slightly larger aBLSCs (most likely totipotent). These cells then develop into yet larger transition cells (trBLSCs), which give rise (likely irreversibly) to ELSCs. ELSCs will then develop (likely irreversibly) to GLLSCs, which then form progenitor cells (likely irreversibly) that are then the source for further differentiated cells. Therefore, it should be recognized that each of the currently known stem cells and progenitor cells are the descendants of a BLSC (typically by differentiation and division).

More specifically, the inventors discovered that BLSCs can be selectively propagated to ELSCs using conditioned ELSC medium (typically defined serum-free). Remarkably, using such medium, substantially all of the BLSCs will progress to ELSCs and then remain ELSCs until further stimulated. So generated ELSCs can then be stimulated with conditioned GLLSC medium (typically defined serum-free). Again, using conditioned GLLSC medium, substantially all of the ELSCs will progress to GLLSCs and then remain GLLSCs until further stimulated (e.g., via dexamethasone or other inductive agents). Using GLLSCs, the inventor subsequently produced numerous cell types following protocols known in the art. Therefore, it should be appreciated that BLSCs according to the inventive subject matter can be cultivated to a desired density/number, and then optionally selectively progressed towards a higher degree of differentiation (e.g., ELSC, GLLSC, progenitor cell, or differentiated cell) in a predictable and controllable fashion. In the inventors' laboratory, and starting from a monoclonal population of BLSCs, 63 different cell types (of over 220 different known cell types in human and rats, including ELSCs and GLSCs) were generated and confirmed by cell surface and/or other markers.

Therefore, and based on the above particular characteristics and advantages, BLSCs may be used as cell therapeutic agents for in vivo tissue regeneration, or may be used as cells for artificial organs ex vivo, which may or may not be implanted into the donor. Such use is especially advantageous as BLSCs can be obtained as true monoclonal cells. For example, stem cells contemplated herein can be used in banking for various therapeutic and/or cosmetic applications. Here the BLSC or other stem cell is isolated from an adult or otherwise post-natal donor and cryopreserved. Optionally, such isolated stem cells can be rendered monoclonal where desired. Upon thawing the stem cells, the cells may be cultivated (and optionally activated, for example, from a suspended to an adherent BLSC) and returned to the donor in an appropriate manner. On the other hand, it is also contemplated that the stem cell recipient need not necessarily be autologous. For example, the door and recipient may be matched by family relationship and/or histocompatibility factors well known in the art.

In further contemplated alternative uses, BLSCs, and especially monoclonal BLSCs may also serve as research tool in the identification and characterization of agents (individual or complex mixtures) that interfere with (e.g., promote or delay) stem cell growth and/or differentiation. The inventors have discovered that human non-embryonic stem cells, and especially BLSCs can be employed as the cell component in a test kit in which multiple containers (e.g., wells in microwell plates) include a predetermined number of preferably monoclonal stem cells, and most preferably monoclonal BLSCs.

Using such assay format, individual compounds, mixtures of compounds, chemical and biological compound libraries, and even serum and fractions thereof can be easily tested for the effect of such compounds on the cells in each well. For example, each well of a 384-well plate can be seeded with $10^2$ to $10^3$ BLSCs in serum-free defined BLSC basal medium (e.g., Moraga MBC-HUB-MEC-100-A002 (human, clinical), MBC-HUB-MED-100-A002 (human, diagnostic), MBC-RTB-MED-100-A002 (rat), MBC-MOB-MED-100-A002 (mouse), MBC-PGB-MED-100-A002 (porcine)). To each well is then added in a desired range of concentrations one or more agents suspected of having influence on stem cell growth (propagation) and/or differentiation. The plated cells are then observed for various parameters, typically including growth and/or differentiation stimulation. The parameters are then correlated with the particular agent or agent(s) to which the cells were exposed.

Such assay will render in a relatively short period a wealth of information of bioactivity of the tested compounds.

It should be especially appreciated that the BLSCs for such test kits will be preferably true monoclonal BLSCs. That is, all of the BLSCs in one test kit will be the offspring of a single BLSC. Consequently, using such true monoclonal cells, stem cell assays will provide accurate information and can even be used for differential analysis, including differential analysis of male versus female BLSC, differential analysis of BLSC from a healthy person versus a non-healthy person, age-dependent differential analysis of BLSCs, or ethnic/race differential analysis of BLSCs. Moreover, while BLSCs are generally preferred, it is also contemplated that such assays can be performed using true monoclonal ELSCs or true monoclonal GLLSCs, which can be cultivated from monoclonal BLSCs (typically using conditioned medium as inducing and maintenance agent). In less preferred aspects, mixtures of BLSCs, ELSCs and GLLSCs are also deemed suitable for use herein.

The inventors still further surprisingly discovered that the BLSCs, and to some degree the ELSCs and/or GLSCs can be stored over extended periods under low oxygen and at elevated temperatures. Therefore, especially preferred multi-well plates will include contemplated stem cells in a gel matrix that is a gel at a temperature below 37° C. For example, such matrix may be formed using gelatin or other suitable gelling/semi-solid agents which may or may not contain Moraga transportation media (e.g., catalog numbers MBC-HUB-MED-100-A004 (human), MBC-RTB-MED-100-A004 (rat), MBC-MOB-MED-100-A004 (mouse), or MBC-PGB-MED-100-A004 (porcine)) or propagation media (e.g. catalog numbers MBC-HUB-MEC-1S00-A006 (human, clinical), MBC-HUB-MED-1S00-A006 (human, diagnostic), MBC-RTB-MED-1S00-A006 (rat), MBC-MOB-MED-1S00-A006 (mouse), MBC-PGB-MED-1S00-A006 (porcine)) at a concentration effective to obtain gelling at temperatures below 35° C. Upon incubation of such plates at 37° C., the gel matrix will turn into a liquid, which can then be replaced with cultivation or other non-gelling medium. Of course, it should be recognized that all contemplated cells may be recombinant (e.g., using artificial chromosomes, or other (transiently or stably transfected) recombinant DNA), include artificial nucleic acid constructs (e.g., siRNA, antisense DNA, etc.), or may be fusion constructs with other cells from the same or a different organism.

Further characterizations, contemplations and procedures are described in our earlier International patent application (serial number PCT/US05/30284, published as WO/2006/028723), which is incorporated by reference herein.

Experiments

The inventors discovered that BLSCs and related stem cells can be isolated from numerous sources using numerous protocols. The following description provides exemplary preferred reagents, materials, and methods to isolate, propagate, and maintain mammalian, and particularly human BLSCs and cells developing from such BLSCs. Furthermore, it should be noted that the stem cells can be harvested not only from human, but also from numerous other non-human sources, especially including mammalian sources (e.g. for veterinary and/or agricultural use, etc.). All materials and reagents are commercially available, and the protocols generally follow good laboratory and manufacture procedures. Unless indicated otherwise, cell and tissue incubations are at 37° C. and 5% $CO_2$.

Harvesting of Adult Stem Cells from Mammalian Whole Blood

One exemplary protocol to obtain adult stem cells from mammalian whole blood includes the following steps: Collect blood under sterile conditions into a vacutainer tube containing EDTA to prevent clotting. Invert tubes several times to ensure proper mixing. Store at 4° C. for predetermined period of time. Add 0.5 ml of Blood to 49.5 mls of Hemolysis solution (Moraga catalog number MBC-ASB-REBG-900A-001) in a 50 ml conical tube. Invert twice to mix. Balance tubes. Centrifuge at 1800×g for 10 minutes. Aspirate off supernatant. Resuspend pellets by agitation, either by stroking across eppendorf tube holder or very gentle vortexing. Reconstitute cell suspension with 2 mls Reconstitution Solution (Moraga catalog number MBC-ASB-REBG-900A-002). Add 1 ml of cells to 49 mls Clarification Solution (Moraga catalog number MBC-ASB-REBG-900A-003) and invert twice to mix. Balance tubes and centrifuge at 1800×g for 10 minutes. Aspirate off supernatant and resuspend pellets by agitation, either by stroking across eppendorf tube holder or very gentle vortexing. Reconstitute with 2 ml Serum-Free Defined BLSC Adherent Propagation Medium (e.g., Moraga catalog numbers MBC-HUB-MEC-1A00-A006 (human, clinical), MBC-HUB-MED-1A00-A006 (human, diagnostic), MBC-RTB-MED-1A00-A006 (rat), MBC-MOB-MED-1A00-A006 (mouse), MBC-PGB-MED-1A00-A006 (porcine) or 2 ml Infusion Solution (e.g., Moraga catalog numbers MBC-ASB-REBG-900A-004 (human), MBC-ASB-REBG-900A-005 (rat), MBC-ASB-REBG-900A-006 (mouse), MBC-ASB-REBG-900A-007 (porcine)). Perform cell counts as described further below.

Harvesting of Adult Stem Cells from Mammalian Tissue

Another exemplary protocol for harvesting adult stem cells from mammalian solid tissues includes the following steps: Harvest tissues from mammals using generally approved procedures. Place tissue "chunks" (<5 $mm^3$) into Transport Media (Moraga Catalog number MBC-HUB-MED-100-A004 (human), MBC-RTB-MED-100-A004 (rat), MBC-MOB-MED-100-A004 (mouse), or MBC-PGB-MED-100-A004 (porcine)). Store at 4° C. for predetermined period of time. Label a 50 ml conical tube. Add Transport Media up to the 5 ml line. Weigh the conical (this is the Tare weight). Under the hood, add enough tissues to fill the conical tube up to the 10 ml line. Weigh the conical (this is the Final weight). Subtracting tare weight from final weight gives weight of tissue. Using sterile conditions, remove about half of the tissue from the conical and place into a 60 mm glass petri dish with a small amount of the Transport Media from the tube. Using small scissors and forceps, mince the tissue into fine pieces the consistency of orange marmalade. Pour this into a fresh (labeled) 50 ml conical tube. Repeat the procedure with the second half of the tissue. This results in approximately 5 mls of tissue per 50 ml conical Add 10 mls of the Serum-Free Defined-Tissue Release Solution (e.g., Moraga catalog numbers MBC-HUB-REC-100-A003 (human, clinical), MBC-HUB-RED-100-A003 (human, diagnostic), MBC-RTB-RED-100-A003 (rat), MBC-MOB-RED-100-A003 (mouse), MBC-PGB-RED-100-A003 (porcine)) to each 50 ml conical. Pour in Transport Media up to the 50 ml line in each conical. Tighten caps and parafilm the cap of each conical. Place inside of a zip-closure plastic bag. Roll up the bag around the conicals and tape the end closed. Place the bag into a Brunswick shaker (or shaker water bath) at 37° C. overnight. Remove the bags from the shaker the next day. Remove the tape from the bags. Disinfect (Moraga catalog number MBC-ASB-MSD-900-A002) the exterior of the bags. Remove the conicals and disinfect the exterior of the conicals. Remove the parafilm from the caps and disinfect the exterior of the conicals a second time.

Spin the conicals at about 25×g for 10 minutes. Check conicals for pelleted tissue chunks. If a pellet is present—pipet the supernatant into a fresh labeled 50 ml conical. Balance the conicals and spin the conicals again at 1800×g for 10 minutes. Pour off supernatant into disinfectant solution (Moraga catalog number MBC-ASB-MSD-900-A001). Resuspend pellets by agitation, either by stroking across eppendorf tube holder or very gentle vortexing conicals. Reconstitute the cells with 2 ml Serum-Free Defined BLSC Adherent Propagation Medium (e.g., Moraga catalog numbers MBC-HUB-MEC-1A00-A006 (human, clinical), MBC-HUB-MED-1A00-A006 (human, diagnostic), MBC-RTB-MED-1A00-A006 (rat), MBC-MOB-MED-1A00-A006 (mouse), MBC-PGB-MED-1A00-A006 (porcine) or 2 ml Infusion Solution (e.g., Moraga catalog numbers MBC-ASB-REBG-900A-004 (human), MBC-ASB-REBG-900A-005 (rat), MBC-ASB-REBG-900A-006 (mouse), MBC-ASB-REBG-900A-007 (porcine)) sequentially.

Measure final volume using a 5 ml pipet—write it down. Remove 15 µl and dilute as necessary for cell counting. Add 15 µl of 0.4% Trypan Blue solution (Moraga catalog number MBC-ASB-MSD-900-A005) to 15 µl of diluted cells and after trituration, place onto a hemocytometer (or Coulter counter). Count the cells and calculate cell numbers. Either plate, infuse or cryopreserve cells as needed.

Harvesting of Adult Stem Cells from Hematocrit

A further alternative manner of obtaining stem cells presented herein includes steps commonly known in hematocrit analysis. Here, the whole blood sample is spun for a cell isolation, wherein the stem cells self-select and sort with the respective hematopoietic fractions. The inventors have observed that the packed red cells contain the ELSCs, the "buffy" coat contains the GLSCs, and the platelet fraction contains the BLSCs.

Standard Procedures for Stem Cell Culture

Plating Cells

Materials and Equipment: Anti-Microbial Sterilization Solutions (Moraga catalog numbers MBC-ASB-MSD-900-A001 and MBC-ASB-MSD-900-A002).

Procedure: Plating Cells (must be performed in Tissue Culture Hood using sterile procedures). Plate cells in Serum-Free Defined Adult Stem Cell Plating Medium (e.g., Moraga catalog numbers MBC-HUB-MEC-900-A008 (human, clinical), MBC-HUB-MED-900-A008 (human, diagnostic), MBC-RTB-MED-900-A008 (rat), MBC-MOB-MED-900-A008 (mouse), MBC-PGB-MED-900-A008 (porcine)). Add ½ volume of medium to precondition culture vessels prior to plating. Plate 500,000 to 1,000,000 cells per T-75 cm2 flask (e.g., Moraga catalog numbers MBC-ASB-MSD-900-A006 (general) MBC-HUB-MSC-900-A006 (human clinical)) in 10 mls medium.

Plate 25,000 to 500,000 cells per T-25 cm2 flask (e.g., Moraga catalog numbers MBC-ASB-MSD-900-A007 (general) MBC-HUB-MSC-900-A007 (human clinical)) in 5 ml medium. Plate 25,000 to 100,000 cells per well per 6-well plate (e.g., Moraga catalog numbers MBC-ASB-MSD-900-A008 (general) MBC-HUB-MSC-900-A008 (human clinical)) in 3 ml medium. Plate 5,000 to 25,000 cells per well per 24-well plate ((e.g., Moraga catalog numbers MBC-ASB-MSD-900-A009 (general) MBC-HUB-MSC-900-A009 (human clinical)) in 1 ml medium. Plate 1,000 to 10,000 cells per well per 48-well plate ((e.g., Moraga catalog numbers MBC-ASB-MSD-900-A010 (general) MBC-HUB-MSC-900-A010 (human clinical)) in 0.5 ml medium. Plate 1,000 to 5,000 cells per well per 96-well plate ((e.g., Moraga catalog numbers MBC-ASB-MSD-900-A011 (general) MBC-HUB-MSC-900-A011 (human clinical)) in 0.2 ml medium. Plate 25,000 to 100,000 cells per 35-mm plate ((e.g., Moraga catalog numbers MBC-ASB-MSD-900-A012 (general) MBC-HUB-MSC-900-A012 (human clinical)) in 3-ml medium. Plate 25,000 to 500,000 cells per 100-mm plate ((e.g., Moraga catalog numbers MBC-ASB-MSD-900-A013 (general) MBC-HUB-MSC-900-A013 (human clinical))) in 5-ml medium.

This represents approximately a 50-70% confluent coverage of the flask surface 18-24 hr after plating. Cell numbers per flask/plate can be increased or decreased accordingly. Place flask/plate in a 37° C. in a 95% air/5% $CO_2$ humidified incubator. After 18-24 hr, check cells. Majority of cells should be attached, although will see some floating dead cells (dark irregular-shaped particulate-appearing) and some floating particulate debris.

Washing Cells

Materials and Equipment: Anti-Microbial Sterilization Solutions (Moraga catalog numbers MBC-ASB-MSD-900-A001 and MBC-ASB-MSD-900-A002). 9¾" borosilicate glass pipettes. Sterile Pipettes. Pipette-Aid. Paper towels/Wipes. Incubator. Phase contrast microscope.

Procedure: Remove plating medium and wash cultures with Sterile Serum-Free Defined BLSC Wash Buffer (e.g., Moraga catalog numbers MBC-HUB-REC-100-A001 (human, clinical), MBC-HUB-RED-100-A001 (human, diagnostic), MBC-RTB-RED-100-A001 (rat), MBC-MOB-RED-100-A001 (mouse), MBC-PGB-RED-100-A001 (porcine)): 2×25 ml for T-75 flasks; 2×13 ml for T-25 flasks; 2×5 ml for 6-well plates; 2×2 ml for 24-well plates; 2×1 ml for 48-well plates; 2×0.2 ml for 96-well plates; 2×5 ml for 35-mm dishes; 2×10 ml for 100-mm dishes Feeding Cells Materials and Equipment: Anti-Microbial Sterilization Solutions (Moraga catalog numbers MBC-ASB-MSD-900-A001 and MBC-ASB-MSD-900-A002). 9¾" borosilicate glass pipettes. Sterile Pipettes. Paper towels/Wipes. Incubator. Phase contrast microscope.

Procedure: Remove wash solution and add designated volume 1 of propagation medium or testing medium to culture vessel, as specified (see below). Feeding (must be performed under sterile tissue culture hood). Open media bottles and leave cap on top of bottle. Place sterile pipettes and 20% disinfectant (MBC-ASB-MSD-900-A001) bottle under the hood. Make sure the Erlenmeyer flask is under the hood and contains bleach. Remove flask/plate from incubator, being sure to close door securely. Carefully place flask/plate under the hood. Wipe contact disinfectant (Moraga catalog number MBC-ASB-MSD-900-A002) over gloved hands. Remove top from flask/plate. Remove spent media from cells. Decant (aspirate) media from flasks into Erlenmeyer flask containing liquid disinfectant (Moraga catalog number MBC-ASB-MSD-900-A001). If decanting, pour over the bottom of the flask to keep cells covered as long as possible. Do not decant all media.

Aspirate about half of spent media from plates (96-well, 48-well, 24-well plates) using vacuum/trap apparatus and glass pipettes. Replace top loosely on flask/plate (lay down flask to keep cells from drying out). Ready plastic graduated pipette. Remove fresh media from bottle (only what you need for one flask/plate at the time). Designated volume of medium used is dependent on the percent confluence of the cells (as visualized with a phase contrast microscope) and the maximal volume of liquid the culture vessel can hold.

The following applies to T-75 flasks, T-25 flasks, 6-well plates, 35-mm dishes, and 100-mm dishes: Cultures should be fed every three days unless otherwise indicated by confluence of cells in the tissue culture vessel. Initial medium feeding after washing should be same volume as original plating medium. For every 10% increase in confluence of the cultures above 70%, double the volume of the medium by adding fresh medium to existing medium during feeding.

Once cells reach 100% confluence the vessel should hold its maximal amount of liquid (i.e., T-25 flask holding 60 ml media). As cells reach 200% confluence replace entire medium volume every two days. As cells reach 300% confluence replace entire medium volume every day. As cells reach 400% confluence replace entire medium volume every 18 hr. As cells reach 500% confluence replace entire medium volume every 12 hr. As cells reach 600% confluence replace entire medium volume every 6 hr. As cells reach 700% confluence replace entire medium volume every 3 hr. Cells can be harvested anytime after 100% confluence.

The following applies for 24-well plates, 48-well plates, and 96-well plates: Cultures should be fed every three days unless otherwise noted (as above). Initial medium feeding after washing should be same volume as original plating medium volume. Replace ½ volume of medium at each feeding. When cultures reach 100% confluence feed every other day. When cultures reach 200% confluence feed every 1.5 days. When cultures reach 300% confluence feed every day. When cultures reach 400% confluence feed every 12 hr. When cultures reach 500% confluence feed every 6 hr. When cultures reach 600% confluence feed every 3 hr. Cells can be harvested anytime after 100% confluence. Testing cells for phenotypic expression markers using antibody microarray enzyme-linked immunoculture assay (ELICA) is best if cultures are <100% confluent.

Suitable Media and Protocols for Feeding Cells

Serum-Free Defined BLSC Adherent Propagation Medium (e.g., Moraga catalog numbers MBC-HUB-MEC-1A00-A006 (human, clinical), MBC-HUB-MED-1A00-A006 (human, diagnostic), MBC-RTB-MED-1A00-A006 (rat), MBC-MOB-MED-1A00-A006 (mouse), MBC-PGB-MED-1A00-A006 (porcine)).

General Induction medium (e.g., Moraga catalog numbers MBC-HUB-IMDG-100-A001 (human), MBC-RTB-IMDG-100-A001 (rat), MBC-MOB-IMDG-100-A001 (mouse), MBC-PGB-IMDG-100-A001 (porcine).

Ectodermal Induction medium (e.g., Moraga catalog numbers MBC-HUB-IMDE-100-A002 (human), MBC-RTB-IMDE-100-A002 (rat), MBC-MOB-IMDE-100-A002 (mouse), MBC-PGB-IMDE-100-A002 (porcine).

Mesodermal Induction medium (e.g., Moraga catalog numbers MBC-HUB-IMDM-100-A003 (human), MBC-RTB-IMDM-100-A003 (rat), MBC-MOB-IMDM-100-A003 (mouse), MBC-PGB-IMDM-100-A003 (porcine).

Endodermal Induction medium (e.g., Moraga catalog numbers MBC-HUB-IMDN-100-A004 (human), MBC-RTB-IMDN-100-A004 (rat), MBC-MOB-IMDN-100-A004 (mouse), MBC-PGB-IMDN-100-A004 (porcine).

Protocol: Loosely replace cap on media bottle. With other hand, remove the top of the flask/plate (carefully angle the flask to one side). Add media to flask/plate. Replace top on flask/plate (tighten securely on flask). Discard pipette into bucket containing liquid disinfectant solution (Moraga catalog number MBC-ASB-MSD-900-A001). Return flask to incubator, being sure to close door securely. Tighten cap on media bottle, remove to counter outside hood, wipe outside of bottle with contact disinfectant solution (Moraga catalog number MBC-ASB-MSD-900-A002) before storage.

Cell Release

Materials and Equipment: Preparation of Anti-Microbial Sterilization Solutions (Moraga catalog numbers MBC-ASB-MSD-900-A001 and MBC-ASB-MSD-900-A002). Contact Disinfectant solution. Pipette tips, 200 µl. Pipettor, 0-200 µl. Hemocytometer. Compound Brightfield Microscope. Sterile pipettes. Pipette-Aid. Polypropylene tubes. 15 ml conicals. Holder for conicals and cell count tubes. Paper towels/Wipes. Weigh balance, double beam. Desktop centrifuge. Timer.

Procedure: Cell Release must be done using sterile conditions within a tissue culture hood. Label 15 ml conical tubes, one tube for each flask harvested. Add two ml of SFD-Cell Release/Activation Solution Inhibitor (e.g., Moraga catalog numbers MBC-HUB-REC-100-A005 (human clinical), MBC-HUB-RED-100-A005 (human, diagnostic), MBC-RTB-RED-100-A005 (rat), MBC-MOB-RED-100-A005 (mouse), MBC-PGB-RED-100-A005 (porcine) to each tube. Remove medium by decanting or aspirating and wash cultures with Sterile Serum-Free Defined BLSC Wash Buffer (e.g., Moraga catalog numbers MBC-HUB-REC-100-A001 (human, clinical), MBC-HUB-RED-100-A001 (human, diagnostic), MBC-RTB-RED-100-A001 (rat), MBC-MOB-RED-100-A001 (mouse), MBC-PGB-RED-100-A001 (porcine)). Rotate flask/plate back and forth, allow to stand for 5 min., remove 1st wash solution.

Repeat with 2nd wash solution with volumes as follows: 2×35 ml for T-75 flasks; 2×13 ml for T-25 flasks; 2×5 ml for 6-well plates; 2×2 ml for 24-well plates; 2×1 ml for 48-well plates; 2×0.2 ml for 96-well plates; 2×5 ml for 35-mm dishes; 2×10 ml for 100-mm dishes;

Remove Sterile Serum-Free Defined BLSC Wash Buffer by decanting or aspirating and incubate cultures for 5 min with Sterile Serum-Free Defined Cell Release Buffer (e.g., Moraga catalog numbers MBC-HUB-REC-100-A002 (human, clinical), MBC-HUB-RED-100-A002 (human, diagnostic), MBC-RTB-RED-100-A002 (rat), MBC-MOB-RED-100-A002 (mouse), MBC-PGB-RED-100-A002 (porcine)) with volumes as follows: 1×25 ml for T-75 flasks; 1×10 ml for T-25 flasks; 1×3 ml for 6-well plates; 1×1 ml for 24-well plates; 1×0.5 ml for 48-well plates; 1×0.1 ml for 96-well plates; 1×3 ml for 35-mm dishes; 1×5 ml for 100-mm dishes;

Remove Sterile Serum-Free Defined Cell Release Buffer by decanting or aspirating and incubate cultures for 0.5 to 5 min with Serum-Free Defined-Cell Release/Activation Solution (e.g., Moraga catalog numbers MBC-HUB-REC-100-

A004 (human, clinical), MBC-HUB-RED-100-A004 (human, diagnostic), MBC-RTB-RED-100-A004 (rat), MBC-MOB-RED-100-A004 (mouse), MBC-PGB-RED-100-A004 (porcine)). Slowly rotate flask/plate back and forth to dislodge cells (takes approximately 0.5-5 min.) with volumes as follows: 1×4 ml for T-75 flasks; 1×3 ml for T-25 flasks; 1×1 ml for 6-well plates; 1×0.5 ml for 24-well plates; 1×0.5 ml for 48-well plates; 1×0.1 ml for 96-well plates; 1×2 ml for 35-mm dishes; 1×3 ml for 100-mm dishes.

When most cells release from flask/plate, triturate cells 5-6 times to ensure good cell suspension. Add cell suspension from each flask to SFD-Cell Release/Activation Inhibitor Solution in a 15 ml conical tube. Wash flask/plate with additional Serum-Free Defined-Cell Release/Activation Solution to dislodge any remaining cells with volumes as follows: 1×4 ml for T-75 flasks; 1×3 ml for T-25 flasks; 1×1 ml for 6-well plates; 1×0.5 ml for 24-well plates; 1×0.5 ml for 48-well plates; 1×0.1 ml for 96-well plates; 1×2 ml for 35-mm dishes; 1×3 ml for 100-mm dishes.

Add solution to tubes and top off to 14 ml with appropriate medium, as necessary and exemplarily listed below. Cap tubes tightly and invert 2-3× to mix cell suspension. Spin at 1800×g for 10 min.

Serum-Free Defined Adult Stem Cell Plating Medium (e.g., Moraga catalog numbers MBC-HUB-MEC-900-A008 (human, clinical), MBC-HUB-MED-900-A008 (human, diagnostic), MBC-RTB-MED-900-A008 (rat), MBC-MOB-MED-900-A008 (mouse), MBC-PGB-MED-900-A008 (porcine))

Serum-Free Defined BLSC Adherent Propagation Medium (e.g., Moraga catalog numbers MBC-HUB-MEC-1A00-A006 (human, clinical), MBC-HUB-MED-1A00-A006 (human, diagnostic), MBC-RTB-MED-1A00-A006 (rat), MBC-MOB-MED-1A00-A006 (mouse), MBC-PGB-MED-1A00-A006 (porcine))

Infusion Solution (e.g., Moraga catalog numbers MBC-ASB-REBG-900A-004 (human), MBC-ASB-REBG-900A-005 (rat), MBC-ASB-REBG-900A-006 (mouse), MBC-ASB-REBG-900A-007 (porcine))

Cryopreservation medium (e.g., Moraga catalog numbers MBC-HUB-MEC-100-A005 (human, clinical), MBC-HUB-MED-100-A005 (human, diagnostic), MBC-RTB-MED-100-A005 (rat), MBC-MOB-MED-100-A005 (mouse), MBC-PGB-MED-100-A005 (porcine))

Cell Counting

Materials and Equipment: Preparation of Anti-Microbial Sterilization Solutions (Moraga catalog numbers MBC-ASB-MSD-900-A001 and MBC-ASB-MSD-900-A002). Contact Disinfectant solution. Pipette tips, 200 µl. Pipettor, 0-200 µl. Hemocytometer. Compound Brightfield Microscope. Sterile pipettes. Polypropylene tubes. 15 ml conicals. Holder for conicals and cell count tubes. Weigh balance, double beam. Desktop centrifuge Procedure: Prepare materials for cell counting. Remove Eppendorf tubes, label, place in cryotube holder, and place in tissue culture hood. Remove hemocytometer from 70% ethanol and dry with Kimwipe. Remove hemocytometer coverslip from 70% ethanol, dry with Kimwipe, place on hemocytometer, and place in TC hood. Remove sterile 0.4% Trypan blue solution and place in TC hood. Remove sterile 200 microliter pipette tips and place in TC hood. Remove 1-200 microliter Rannin pipettor, wipe white end of pipettor with contact disinfectant solution to sterilize, and place in TC hood. Aspirate supernatant leaving approximately 0.1-0.3 ml with cell pellet. Look at size of cell pellet, approximate size to multiples of 0.25 ml. Resuspend cell pellet in residual supernatant by stroking across (eppendorf) cryovial holder (6-10×). Resuspend cells in fresh medium 1:1 with resuspended cell pellet, triturate until cell suspension homogeneous.

Suitable Media Include:

Serum-Free Defined Adult Stem Cell Plating Medium (e.g., Moraga catalog numbers MBC-HUB-MEC-900-A008 (human, clinical), MBC-HUB-MED-900-A008 (human, diagnostic), MBC-RTB-MED-900-A008 (rat), MBC-MOB-MED-900-A008 (mouse), MBC-PGB-MED-900-A008 (porcine))

Serum-Free Defined BLSC Adherent Propagation Medium (e.g., Moraga catalog numbers MBC-HUB-MEC-1A00-A006 (human, clinical), MBC-HUB-MED-1A00-A006 (human, diagnostic), MBC-RTB-MED-1A00-A006 (rat), MBC-MOB-MED-1A00-A006 (mouse), MBC-PGB-MED-1A00-A006 (porcine))

Infusion Solution (e.g., Moraga catalog numbers MBC-ASB-REBG-900A-004 (human), MBC-ASB-REBG-900A-005 (rat), MBC-ASB-REBG-900A-006 (mouse), MBC-ASB-REBG-900A-007 (porcine))

Measure reconstituted volume. Remove 15 microliters of cell suspension with sterile pipettor and place into eppendorf tube. Add 15 microliters of sterile 0.4% Trypan blue (using Rannin 1-200 microliter pipettor) to eppendorf tube and triturate 5-6 times, place drop of cell suspension/Trypan blue on hemocytometer (in groove). Count cells. [On hemocytometer, count all cells within the nine large grids, then average the cell number per each large grid]. The formula to determine cell number is $[(((\text{average number})/5)/5) \times 0.25) \times 2] = \text{cells} \times 10^6$ cells per ml.

The cells can be identified as follows: Suspended BLSCs—trypan blue positive. Adherent BLSCs—trypan blue positive. Transition BLSCs—trypan blue positive periphery, clear/refractile center. ELSCs—trypan blue negative, clear/refractile cells. Transition ELSCs—trypan blue negative, clear/refractile cells. GLSCs—trypan blue negative, clear/refractile cells. Transition GLSCs—trypan blue negative, clear/refractile cells. Progenitor cells—trypan blue negative, clear/refractile cells. Differentiated cells—trypan blue negative, clear/refractile cells.

An alternate formula that can be used to determine cell number per ml is the average number (above) divided by 50, i.e., $[(\text{average number})/50] = \text{cells} \times 10^6$ cells per ml. A third alternate formula that can be used to determine cell number per ml is the average number (above) $\times 2 = \text{cells} \times 10^4$ cells per ml. The three formulas are equivalent to each other. This number can then be multiplied by the total reconstituted volume to determine total number of cells harvested. However, when ready to plate, you need to figure in the number of cells removed in the 15 microliter sample for cell counting. Cells can be either be plated, screened by flow cytometry, sorted by flow cytometry, cryopreserved, or discarded.

Cryopreservation

Materials and Equipment: Cell Release. Serum-Free Defined Adult Stem Cell Plating Medium (e.g., Moraga catalog numbers MBC-HUB-MEC-900-A008 (human, clinical), MBC-HUB-MED-900-A008 (human, diagnostic), MBC-RTB-MED-900-A008 (rat), MBC-MOB-MED-900-A008 (mouse), MBC-PGB-MED-900-A008 (porcine)). Cryopreservation medium (e.g., Moraga catalog numbers MBC-HUB-MEC-100-A005 (human, clinical), MBC-HUB-MED-100-A005 (human, diagnostic), MBC-RTB-MED-100-A005 (rat), MBC-MOB-MED-100-A005 (mouse), MBC-PGB-MED-100-A005 (porcine)). Freezing Chamber. Cryovials, 2.0 ml. −70° C. Freezer and −80° C. Freezer. Nalgene Cryobox.

Procedure: Cryopreservation of Stem Cells (cell manipulation must be performed in sterile tissue culture hood). Count cells (see cell count procedure, need only count cells once). Resuspend cells at 2 to 24×10$^6$ cells per ml in species-specific Serum-Free Defined Adult Stem Cell Plating Medium. Aliquot 0.5 ml cell suspension to sterile cryovial. Add equal volume of species-specific cryopreservation medium to cryovial. Note that the cryoprotectant is toxic to the cells at ambient temperature (liquid state). Therefore, handle the cells very gently and try to minimize the time the cells are in ambient temperature cryopreservation medium, both during the cryopreservation procedure and subsequent thaw and plating procedure.

Cap tube tightly and invert, slowly 2×, to mix contents. Immediately place in freezing chamber (containing isopropyl alcohol) and place freezing chamber into Revco for slow freezing to storage at −70° C.±5° C. for GLLSCs; −70° C.±5° C. for transitional ELSCs; −80° C.±5° C. for ELSCs; −80° C.±5° C. for transitional BLSCs; −80° C.±5° C. for adherent BLSCs; −80° C.±5° C. for suspended BLSCs. After 24 to 48 hr remove cryovials from freezing chamber, place in Nalgene cryobox and store in Revco (appropriate temperature) until use.

Thawing & Cell Reconstitution for Plating

Materials and Equipment: Preparation of Anti-Microbial Sterilizing Solutions. Species-specific Serum-Free Defined Adult Stem Cell Plating Medium (e.g., Moraga catalog numbers MBC-HUB-MEC-900-A008 (human, clinical), MBC-HUB-MED-900-A008 (human, diagnostic), MBC-RTB-MED-900-A008 (rat), MBC-MOB-MED-900-A008 (mouse), MBC-PGB-MED-900-A008 (porcine)). Pipet tips, 100 microliter. Pipettor, 0-200 µl. Hemocytometer. Compound Brightfield Microscope. Sterile pipets. Pipet-Aid. Polypropylene tubes. 15 ml conicals. Holders for conicals and cell count tubes. Weigh Balance, double beam. Desktop Centrifuge. Incubator Procedure: Plating Cells from Cryopreserved Stocks (must be performed in TC Hood): Label 15 ml conical tubes, 1 per cryovial. Add 12 ml of Species-specific Serum-Free Defined Adult Stem Cell Plating Medium to each tube. Remove desired cryovials from freezer. Allow thawing to ambient temperature (either slow thaw by sitting cryovial out in hood, quick thaw by placing cryovial in palm of hand and rubbing hands together quickly, or quick thaw by placing in 37° C. water bath). Add thawed cell suspension slowly (drop wise) to medium in 15 ml conical tube. Cap tightly and invert tube slowly 2× to mix contents. Balance conicals in centrifuge buckets. Spin at 1800×g for 10 min. Decant (or aspirate) supernatant leaving approximately 0.1-0.3 ml with cell pellet. Look at size of cell pellet, approximate size to multiples of 0.25 ml. Resuspend cell pellet in residual supernatant by stroking across cryovial holder (6-10×). Resuspend cells in fresh medium 1:1 with resuspended cell pellet, triturate until cell suspension homogeneous. Triturate until cell suspension homogeneous. Measure reconstituted volume. Remove 15 microliters of cell suspension with sterile pipettor and place into eppendorf tube. Add 15 microliters of sterile 0.4% Trypan blue (using Rannin 1-200 microliter pipettor) to eppendorf tube and triturate 5-6 times, place drop of cell suspension/Trypan blue on hemocytometer (in groove).

Count cells. [On hemocytometer, count all cells within the nine large grids, then average the cell number per each large grid]. The formula to determine cell number is [(((average number)/5)/5)×0.25)×2]=cells×10$^6$ cells per ml. As above, cells can be identified as follows: Suspended BLSCs—trypan blue positive. Adherent BLSCs—trypan blue positive. Transition BLSCs—trypan blue positive periphery, clear/refractile center. ELSCs—trypan blue negative, clear/refractile cells. Transition ELSCs—trypan blue negative, clear/refractile cells. GLSCs—trypan blue negative, clear/refractile cells. Transition GLSCs—trypan blue negative, clear/refractile cells. Progenitor cells—trypan blue negative, clear/refractile cells. Differentiated cells—trypan blue negative, clear/refractile cells.

An alternate formula that can be used to determine cell number per ml is the average number (above) divided by 50, i.e., [(average number)/50]=cells×10$^6$ cells per ml. A third alternate formula that can be used to determine cell number per ml is the average number (above)×2=cells×10$^4$ cells per ml. The three formulas are equivalent to each other. This number can then be multiplied by the total reconstituted volume to determine total number of cells harvested. However, when ready to plate, you need to figure in the number of cells removed in the 15 microliter sample for cell counting. Cells can be plated, screened by flow cytometry, sorted by flow cytometry, cryopreserved, or discarded.

Thus, specific embodiments and applications of non-embryonic totipotent blastomere-like stem cells have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein, is inconsistent or contrary to the definition of that term provided herein, the definition of that term provided herein applies and the definition of that term in the reference does not apply.

What is claimed is:

1. A method of isolating a post-natal pluripotent or totipotent stem cell that lacks trypan blue exclusion and is viable to proliferate in serum-free medium, comprising:
   providing a tissue sample and placing the tissue sample into a first serum-free medium;
   incubating the tissue sample for a time sufficient to (a) allow non-stem cells in the tissue sample to die and to (b) maintain viability of the stem cell in the sample; and
   processing the tissue in a second serum-free medium to enrich or isolate the stem cell, wherein first and second serum-free media employ a carbohydrate source other than glucose, and wherein the stem cell proliferates in the second serum-free medium.

2. The method of claim 1 wherein the tissue sample comprises whole blood or a mechanically and enzymatically treated solid tissue.

3. The method of claim 1 wherein the incubation time is at least 5 days at about 4 C to thereby enrich or isolate an ELSC.

4. The method of claim 1 wherein the incubation time is at least 7 days at about 4 C to thereby enrich or isolate an adherent BLSC.

5. The method of claim 1 wherein the incubation time is at least 9 days at about 4 C to thereby enrich or isolate a suspended BLSC.

6. The method of claim 1 wherein the stem cell has an average size of equal or less than 5 micrometer.

* * * * *